(12) United States Patent
Nishiyama

(10) Patent No.: US 10,893,925 B2
(45) Date of Patent: Jan. 19, 2021

(54) INSTRUMENT FOR PREVENTING MALE URINARY INCONTINENCE AND COVER

(71) Applicant: Tetsuryuu Nishiyama, Ishikawa (JP)

(72) Inventor: Tetsuryuu Nishiyama, Ishikawa (JP)

( * ) Notice: Subject to any disclaimer, the term of this patent is extended or adjusted under 35 U.S.C. 154(b) by 0 days.

(21) Appl. No.: 16/771,197

(22) PCT Filed: Aug. 30, 2019

(86) PCT No.: PCT/JP2019/034119
§ 371 (c)(1),
(2) Date: Jun. 9, 2020

(65) Prior Publication Data
US 2020/0397553 A1 Dec. 24, 2020

(30) Foreign Application Priority Data
Jun. 18, 2019 (JP) .................................. 2019-112515

(51) Int. Cl.
*A61F 2/00* (2006.01)
(52) U.S. Cl.
CPC .... *A61F 2/0054* (2013.01); *A61F 2220/0008* (2013.01)
(58) Field of Classification Search
CPC ...... A61F 2/0054; A61F 2/004; A61F 2/0031; A61F 2/0027; A61F 2/0004; A61F 2/26;
(Continued)

(56) References Cited

U.S. PATENT DOCUMENTS 4,942,886 A * 7/1990 Timmons ............. A61B 17/132
128/885

6,039,750 A * 3/2000 Kubalak ............... A61F 2/0054
128/DIG. 25
(Continued)

FOREIGN PATENT DOCUMENTS

JP 51-31094 A 3/1976
JP 58-175554 A 10/1983
(Continued)

OTHER PUBLICATIONS

International Search Report and Written Opinion for corresponding Application No. PCT/JP2019/34119, dated Nov. 19, 2019.
(Continued)

*Primary Examiner* — Tarla R Patel
(74) *Attorney, Agent, or Firm* — Renner, Otto, Boisselle & Sklar, LLP

(57) ABSTRACT

A urinary incontinence prevention instrument for males includes: an annular part made by forming a portion of a belt-like component; a convex part for pressing the urethra attached to the inner circumference surface side of the annular part; an adjustment mechanism for adjusting the diameter of the annular part; and a pinching-prevention component having a hole for passing the belt-like component, a lower part of the pinching-prevention component is positioned between the penis and the adjustment mechanism, preventing the skin of the penis from being pinched in the adjustment mechanism, the adjustment mechanism is located inside the hole, and both ends of the belt-like component pass through the inside of the hole and penetrate an upper part of the pinching-prevention component, the lower part of the pinching-prevention component and the convex part for pressing the urethra are at positions facing each other with the penis sandwiched in between.

4 Claims, 4 Drawing Sheets

(58) Field of Classification Search
CPC .................. A61F 5/41; A61F 2005/411; A61F 2005/412; A61F 2005/414; A61F 2005/415; A61F 2005/417; A61F 2005/418; A61F 2013/15121; A61F 13/471; A61H 19/00; A61H 19/32; A61H 19/30
See application file for complete search history.

(56) References Cited

U.S. PATENT DOCUMENTS

2008/0011310 A1    1/2008  Anderson
2016/0367349 A1*  12/2016  Williams .............. A61F 2/0036

FOREIGN PATENT DOCUMENTS

| JP | 6092457 B | 3/2017 |
| WO | 9814146 A1 | 4/1998 |
| WO | 9955251 A1 | 11/1999 |

OTHER PUBLICATIONS

Decision to Grant Patent in corresponding Japanese Patent Application No. 2019-112515, dated Aug. 16, 2019.

* cited by examiner

[Fig.1]
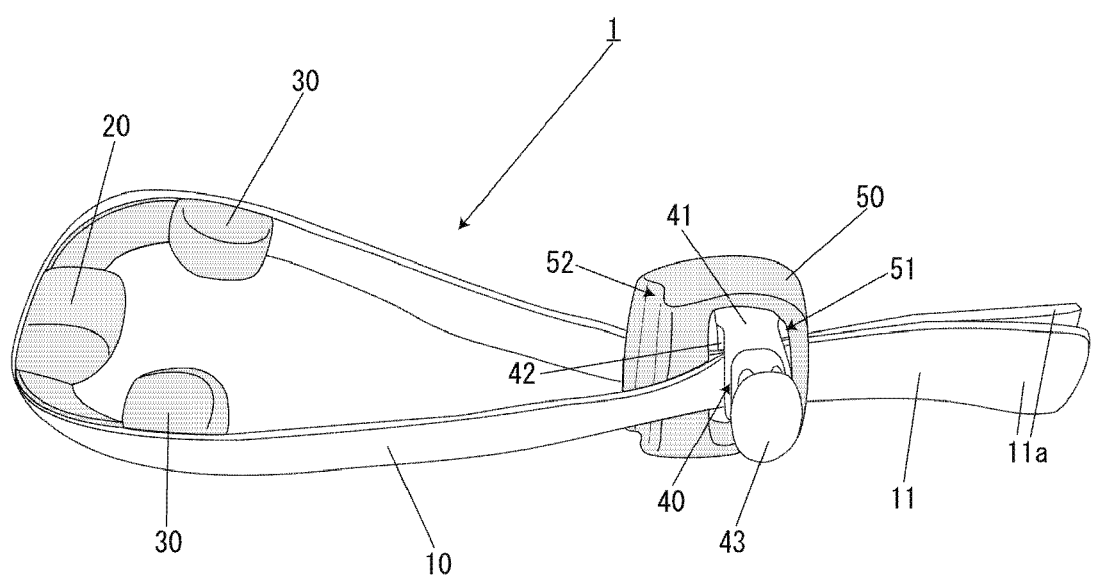

[Fig.2]
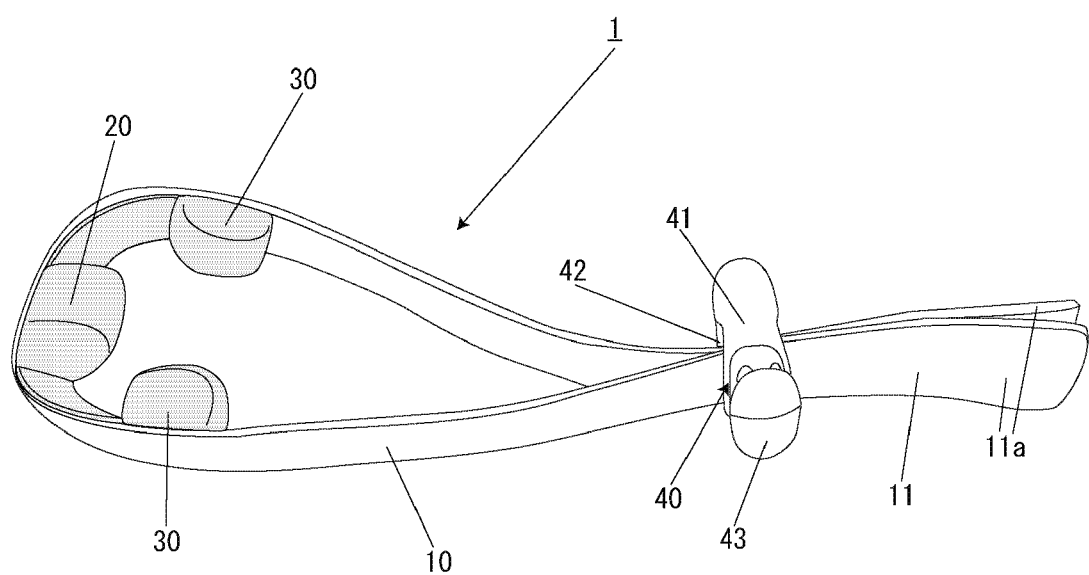

[Fig.3]
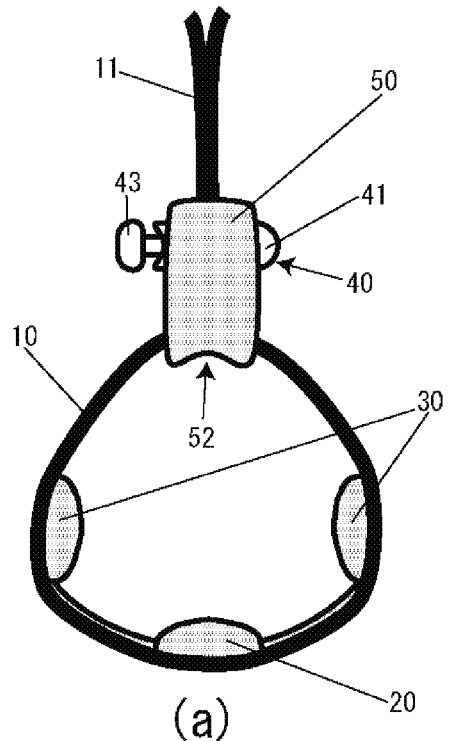
(a)
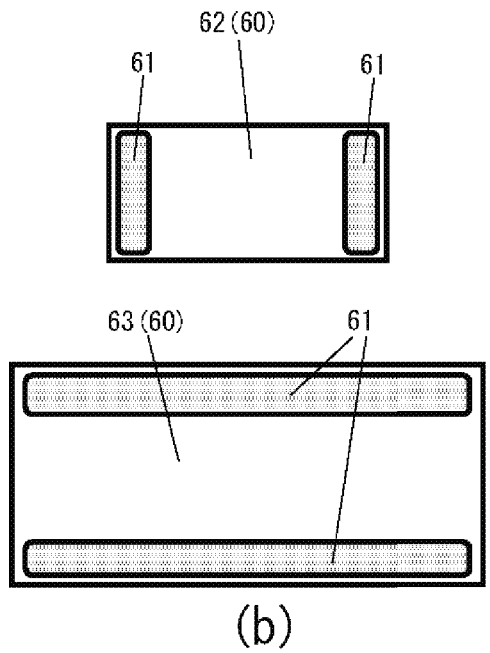
(b)
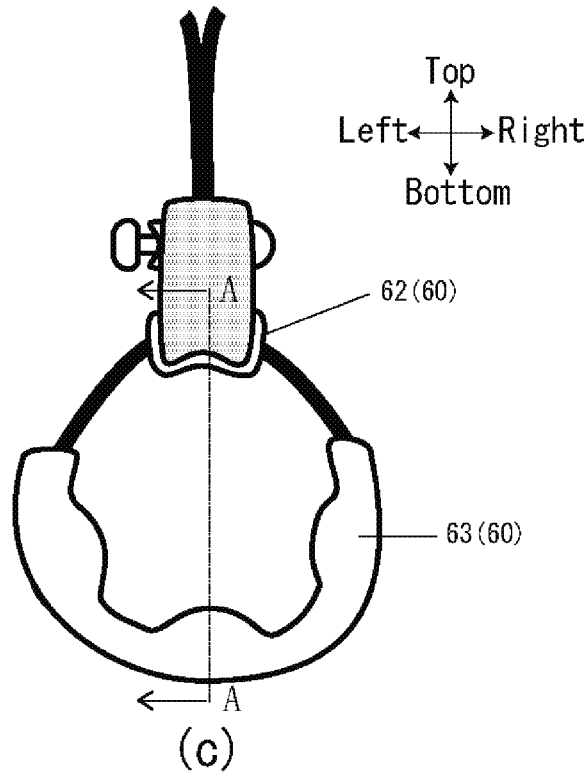
(c)
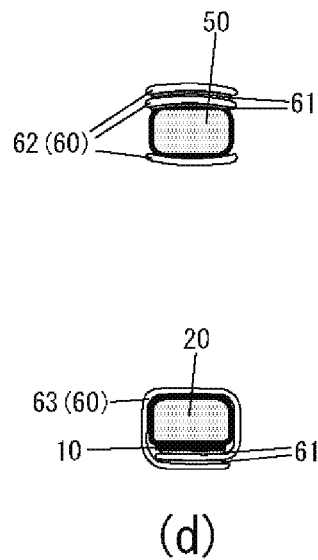
(d)

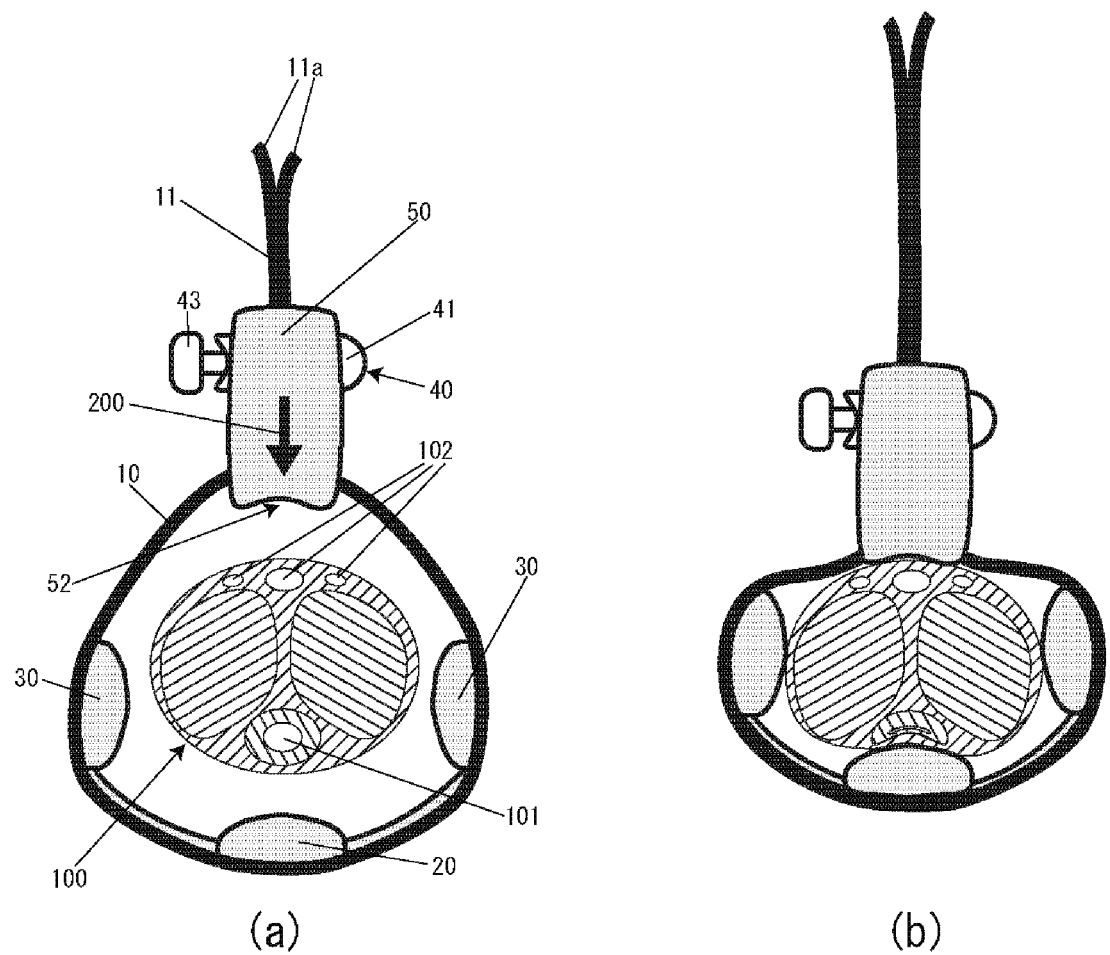
[Fig.4]

INSTRUMENT FOR PREVENTING MALE URINARY INCONTINENCE AND COVER

TECHNICAL FIELD

The present invention relates to a urinary incontinence prevention instrument for males and a cover for the instrument, which is safe and sanitary, and can be easily and accurately worn while preventing pinching of the skin.

BACKGROUND

There are various causes of urinary incontinence in males. For example, aging, prostatic hyperplasia, prostate cancer, as well as neurological symptoms such as multiple sclerosis, Parkinson's disease and Alzheimer's disease, diabetes and obesity, which are problems common to many people.

Instruments for preventing urinary incontinence for males have been known as disclosed in Patent Documents 1 to 3.

All of these instruments are ring-shaped with a part opened and have a convex part at the lower part of their inner circumference. A urethra is located in the mid-lower part of the penis and extends from its root to its tip. user inserts the penis into an opening of the instrument while expanding the opening and tightens the opening while keeping the convex part in contact with the urethra. Since the urethra is pushed and obstructed by the convex part, urinary incontinence is prevented.

However, the technologies disclosed in Patent Documents 1 to 3 have the following problems.

When the opening is tightened, one end of the ring moves along the inner surface of the opposite end. At that time, the skin of the penis is pinched in the gap between the one end and the opposite end, and some pain or injury for the user might be caused. Such skin-pinching-problems also occur when the penis changes in size while the instrument is attached to the penis or when the penis moves in the anteroposterior direction.

In Patent Document 1, the skin-pinching-problem is solved by attaching a pad made of sponge or the like to the inner circumference surface(see [0063], FIGS. 12 and 13 of Patent Document 1). However, there is a sanitary problem that urine soaks into the pad, or the skin steams due to decrease of air permeability.

In addition, when the opening is tightened with the convex portion in contact with the lower part of the urethra, the position of the convex portion gradually shifts from the urethra. This problem appears prominently when the instrument is attached to the penis with only one hand as shown in Patent Document 1(see [0016]of Patent Document 1).

Additionally, when the entire internal circumferential surface of the instrument adheres closely to the penis, the blood flow in the penis is decreased and makes it difficult to secure a sufficient amount of blood flow.

The inventor of the present application has invented a urinary incontinence prevention instrument for males in consideration of the previously mentioned problems, as in Patent Document 4.

The instrument has an annular part made by annularly forming a portion of a belt-like component, a convex part for pressing the urethra, an adjustment mechanism for adjusting a diameter of the annular part and a pinching-prevention component having a hole for passing the belt-like component. The user can prevent the skin of the penis from being pinched in the adjustment mechanism by positioning the pinching-prevention component between the penis and the adjustment mechanism.

CITATION LIST

Patent literature

Patent Document 1: Japanese Unexamined Patent Application Publication No. 2002-512841
Patent Document 2: Japanese Unexamined Patent Application Publication No. 2001-501116
Patent Document 3: Japanese Unexamined Patent Application Publication No. 58-175554
Patent Document 4: Japanese Patent Application No. 6092457

SUMMARY OF INVENTION

Technical problem

However, experiments by the inventor of the present application have revealed that the instrument of Patent Document 4 may still cause urinary incontinence. To reliably prevent incontinence, an upward force must be applied to the urethra from the convex part positioned just below the urethra. When the user wears the instrument for a certain period of time, the pinching-prevention component may fluctuate or its position may slightly shift. As a result of the fluctuation or shift, the upward force acting on the urethra from the convex part is weakened or the force is applied diagonally to the urethra, whereby urinary incontinence is caused.

The object of the present invention is to provide a urinary incontinence prevention instrument for males and a cover, that are safe and sanitary, and can be easily and accurately worn while preventing pinching of the skin of the penis.

Solution to the Problem

To achieve the aforementioned objective, an aspect of the present invention provides a urinary incontinence prevention instrument for males, comprising: an annular part made by annularly forming a portion of a belt-like component; a convex part for pressing the urethra, the convex part being attached to the inner circumference surface side of the annular part; an adjustment mechanism for adjusting the diameter of the annular part; and a pinching-prevention component having a hole for passing the belt-like component, a lower part of the pinching-prevention component is positioned between the penis and the adjustment mechanism, preventing the skin of the penis from being pinched in the adjustment mechanism, the adjustment mechanism is located inside the hole, and both ends of the belt-like component pass through the inside of the hole and penetrate an upper part of the pinching-prevention component, the lower part of the pinching-prevention component and the convex part for pressing the urethra are at positions facing each other with the penis sandwiched in between.

Another aspect of the present invention is to be provided with a plurality of convex parts for the spacer that are attached to the inner circumference surface of the annular part to form a gap between the penis and the inner circumference surface of the annular part.

Yet another aspect of the present invention is that the adjustment mechanism changes the lengths of both ends of the belt-like component by the same amount.

A final aspect of the present invention provides a cover used for the urinary incontinence prevention instrument for males, comprising: an adhesive portion, being fixed to the pinching-prevention component or the convex part for pressing the urethra by using the adhesive portion.

Advantages Effects of Invention

In the present invention, the adjustment mechanism is located inside the hole, and both ends of the belt-like component pass through the inside of the hole and penetrate the upper portion of the pinching-prevention component. Since the upper part of the pinching-prevention component is fixed to the belt-like component, the lower part of the pinching-prevention component and the convex part for pressing the urethra can be kept in a state of being opposed to each other with the penis interposed therebetween. While the user wears the urinary incontinence prevention instrument, the upward force continues to act on the urethra from the convex part for pressing the urethra, and the upward force is received by the lower part of the pinching-prevention component. Thus, the urethral sealing condition can be reliably maintained for a long period of time and incontinence can be prevented.

In addition, the pinching-prevention component can prevent the skin of the penis from being pinched by the adjustment mechanism, and thus the safety of the user is ensured.

By providing the convex part for the spacer, a gap is formed between the penis and the inner circumferential surface of the annular part. The gap ensures blood flow and air permeability of the penis, and safety and sanitation are ensured.

When the adjustment mechanism has a function of changing the length of both ends of the belt-like component by the same amount, during the time the user is adjusting the diameter of the annular part, the position of the convex part for pressing the urethra does not move from the lower portion of the annular part. So, the user can easily and accurately wear the urinary incontinence prevention instrument for males with only one hand keeping the state of the convex part for pressing the urethra in contact with the urethra.

Further, if the cover is detachably fixed to the annular part by using the adhesive portion, the user can easily replace the cover when it becomes dirty and maintain a clean state.

BRIEF DESCRIPTION OF DRAWINGS

FIG. 1 is a perspective diagram illustrating the appearance of a urinary incontinence prevention instrument for males.

FIG. 2 is a perspective diagram illustrating the appearance of the urinary incontinence prevention instrument for males (not drawing a pinching-prevention component).

FIG. 3A is a front view of the urinary incontinence prevention instrument for males. FIG. 3B is a front view of the appearance of a cover. FIG. 3C is a front view of the urinary incontinence prevention instrument for males to which the cover is attached. FIG. 3D is a view as seen from the arrow A-A of FIG. 3C.

FIG. 4 is a front view illustrating the usage of the urinary incontinence prevention instrument for males. FIG. 4A shows the state before the urinary incontinence prevention instrument for males is tightened by the adjustment mechanism. FIG. 4B shows the state when the urinary incontinence prevention instrument for males is tightened.

DESCRIPTION OF EMBODIMENTS

The embodiments of a urinary incontinence prevention instrument for males of the present invention will be explained.

As illustrated in FIGS. 1-3, the urinary incontinence prevention instrument for males 1 includes an annular part 10, a convex part for pressing the urethra 20, a convex part for the spacer 30, an adjustment mechanism 40, a pinching-prevention component 50 and a cover 60. FIGS. 1, 2 and 4 do not draw the cover 60 to facilitate understanding of the structure of the urinary incontinence prevention instrument for males 1, and further FIG. 2 does not draw a pinching-prevention component 50. The annular part 10 is made by annularly forming a portion of the belt-like component 11.

The material of the belt-like component 11 is not limited; for example, a woven fabric, nonwoven fabric, synthetic resin or paper may be used.

As illustrated in FIG., 4, the convex part for pressing the urethra 20 is a component to press the urethra 101. The urethra 101 is located in the mid-lower part of the penis 100, so the convex part for pressing the urethra 20 is attached to a lower part of the inner circumferential surface of the annular part 10.. The convex part for pressing the urethra 20 is preferably formed of a material such as silicone rubber or sponge which is elastically deformable and has water resistance.

The convex part for the spacer 30 is to form a gap between the penis 100 and the inner circumference surface of the annular part 10. In this embodiment, the two convex parts for the spacer 30 are attached to the inner circumference surface of the annular part 10, but the three or more convex parts for the spacer 30 may be attached. The convex part for pressing the urethra 20 and the convex part for the spacer 30 may be integrally formed, and further, the convex part for pressing the urethra 20, the convex part for the spacer 30 and the belt-like component 11 may be integrally formed.

The shapes of the convex part for pressing the urethra 20 and the convex part for the spacer 30 are not limited. If the shapes of the convex part for pressing the urethra 20 and the convex part for the spacer 30 are hemispherical, the convex part for pressing the urethra 20 and the convex part for the spacer 30 come into contact with the penis 100 on their spherical surface. Such a hemispherical shape is preferable because stimulation to the penis 100 is suppressed, and the user can wear the urinary incontinence prevention instrument for males 1 for a long period of time.

INDUSTRIAL APPLICABILITY

The adjustment mechanism 40 is to adjust a diameter of the annular part 10. The adjustment mechanism 40 of the present embodiment includes a tubular body 41, a slit 42 formed in a part of the tubular body 41, a stopper (not shown) stored in the tubular body 41 in a state of being spring-biased so as to be movable in the direction of closing the slit 42, and a button 43 provided for moving the stopper against the spring force.

When the user presses the button 43, the slit 42 is opened and the belt-like component 11 becomes movable in the slit 42. On the other hand, when the button 43 is released, the stopper moves by the spring force in the direction of closing the slit 42 and presses the belt-like component 11 so that it cannot move. The user can adjust the diameter of the annular part 10 by adjusting the position of the adjustment mechanism 40 while pressing the button 43.

According to this adjustment mechanism 40, when adjusting the diameter of the annular part 10, the lengths of both ends of the belt-like component 11 change by the same amount, so the position of the convex part for pressing the urethra 20 does not move from the lower portion of the annular part 10. Therefore, it is possible to accurately maintain the state of the convex part for pressing the urethra 20 kept in contact with the urethra 101 while the user reduces the diameter of the annular part 10.

The pinching-prevention component 50 is a member for preventing the skin of the penis 100 from being pinched by the adjustment mechanism 40 through having its lower portion located between the penis 100 and the adjustment mechanism 40.

The pinching-prevention component 50 has a hole 51 through which the belt-like component 11 passes. The pinching-prevention component 50 is made of silicone.

The shape of the pinching-prevention component 50 is not limited and may be circular or polygonal. The shape of the pinching-prevention component 50 may be a plate having the hole 51 formed in a part thereof. The material of the pinching-prevention component 50 is not limited to silicone, and may be synthetic resin, wood, or metal.

The adjustment mechanism 40 is located inside the hole 51, and both ends 11a of the belt-like component 11 pass through the inside of the hole 51 and penetrate the upper part of the pinching-prevention component 50. The pinching-prevention component 50 is fixed to the belt-like component 11 at its upper portion. Therefore, the lower part of the pinching-prevention component 50 and the convex part for pressing the urethra 20 can be maintained at a position where they are always opposed to each other with the penis 100 interposed therebetween. While the user wears the urinary incontinence prevention instrument for males 1 on the penis 100, an upward force from the convex part for pressing the urethra 20 continues to act on the urethra 101, and the upward force is received by the lower part of the pinching-prevention component 50. Thus, the sealing condition of the urethra 101 can be maintained for a long period of time.

A curved portion 52 may be provided at the lower part of the pinching-prevention component 50. The center of the curved portion 52 is curved upward. Since the upper part of the penis 100 comes in contact along the curve, it is possible to prevent the pinching-prevention component 50 from wobbling or coming off from the penis 100.

The cover 60 is a detachable member to cover the periphery of the annular part 10. The cover 60 has an adhesive portion 61. An upper cover 62 of the cover 60 is fixed by using the adhesive portion 61 in a state of covering the upper portion of the annular part 10. A lower cover 63 of the cover 60 is fixed by using the adhesive portion 61 in a state of covering the lower portion of the annular part 10, which is the convex part for pressing the urethra 20 and the convex part for the spacer 30. When the urinary incontinence prevention instrument for males 1 is used more than once, the cover 60 becomes dirty, so the user can replace the cover 60 at an appropriate timing. The cover 60 may be made of a non-woven fabric, gauze, or cloth.

Next, a method of using the urinary incontinence prevention instrument for males 1 will be explained.

The user opens the slit 42 by pressing the button 43 of the adjustment mechanism 40, and moves the adjustment mechanism 40 to both ends 11a of the belt-like component 11 to increase the diameter of the annular part 10 in advance.

Next, as shown in FIG. 4 (a), the penis 100 is inserted into the annular part 10 in a state where the convex part for pressing the urethra 20 is located at the lowest position. The lower part of the pinching-prevention component 50 is always located at a position facing the convex part for pressing the urethra 20 with the penis 100 interposed therebetween.

Next, the user moves the adjustment mechanism 40 to the annular part 10 side (the direction of arrow 200 in FIG. 4 (a)) while pressing the button 43 to reduce the diameter of the annular part 10. The user tightens the adjustment mechanism 40 until the upper portion of the penis 100 contacts the curved portion 52 and the convex part for pressing the urethra 20 appropriately presses the urethra 101. At this time, for example, the user presses the button 43 with the thumb of the right hand, supporting the tubular body 41 with the index finger. And the user pulls both ends 11a of the belt-like component 11 with the ring finger and the little finger while moving the thumb and index finger in the direction of arrow 200. Then, the user can move the adjustment mechanism 40 with only one hand. Since the adjustment mechanism 40 can be moved by one hand, even if one of the user's two hands is unavailable, the user can wear the urinary incontinence prevention instrument for males 1 with only one hand.

Since the pinching-prevention component 50 continues to be located between the penis 100 and the adjustment mechanism 40 while the diameter of the annular part 10 is reduced, the skin of the penis 100 is not pinched in the adjustment mechanism 40.

When the urinary incontinence prevention instrument for males 1 is attached to the penis 100 as shown in FIG. 4(b), the urethra 101 is appropriately pressed by the convex part for pressing the urethra 20, and the convex part for the spacer 30 makes a proper gap between the penis 100 and the inner circumferential surface of the annular part 10. Thus, the air permeability of the skin of the penis 100 and the blood flow of the blood vessel 102 can be secured while preventing urinary incontinence.

The lower part of the pinching-prevention component 50 is always positioned with the penis 100 sandwiched and opposed to the convex part for pressing the urethra 20 while the urinary incontinence prevention instrument for males 1 is attached to the penis 100, so the skin of the penis 100 is not pinched between the adjustment mechanism 40. Furthermore, with the passage of time, the position of the pinching-prevention component 50 is not shifted. And the adjustment mechanism 40 unintentionally moves to both ends 11a side of the belt-like component 11, the diameter of the annular part 10 is not loosened or increased.

The user may appropriately adjust the tightening strength according to the situation, such as tightening the urinary incontinence prevention instrument for males 1 more strongly when performing manual work or loosely adjusting the urinary incontinence prevention instrument for males 1 when sitting or sleeping in bed.

Although the urinary incontinence prevention instrument for males 1 includes the convex part for the spacer 30 in the present embodiment, the blood flow of the blood vessel 102 can be ensured without the convex part for the spacer 30 if the belt-like component 11 is made of a material having high breathability or a material having high flexibility.

In addition, although the adjustment mechanism 40 changes the length of both ends of the belt-like component 11 by the same amount, not limited thereto, for example, the diameter of the annular part 10 may be changed by pulling only one end of the belt-like component 11 like a belt buckle. In this case, caution should be exercised so that the convex part for pressing the urethra 20 accurately comes in contact with the urethra 101.

INDUSTRIAL APPLICABILITY

The present invention relates to an instrument for a urinary incontinence prevention instrument for males and a cover, which are safe and sanitary, and which can be easily and accurately worn while preventing pinching of the skin of the penis. The invention is therefore applicable to the industry.

REFERENCE SIGN LIST 1 urinary incontinence prevention instrument for males
10 annular part
11 belt-like component
11a both ends
20 convex part for pressing the urethra
30 convex part for the spacer
40 adjustment mechanism
41 tubular body
42 slit
43 button
50 pinching-prevention component
51 hole
52 curved portion
60 cover
61 adhesive portion
62 upper cover
63 lower cover
100 penis
101 urethra
102 blood vessel

The invention claimed is:

1. A urinary incontinence prevention instrument for males, comprising:
    an annular part made by annularly forming a portion of a belt-like component;
    a convex part for pressing a urethra of a penis, the convex part being attached to an inner circumference surface side of the annular part;
    an adjustment mechanism for adjusting a diameter of the annular part; and
    a pinching-prevention component having a hole for passing the belt-like component,
    wherein a lower part of the pinching-prevention component is positioned between the penis and the adjustment mechanism, preventing a skin of the penis from being pinched in the adjustment mechanism,
    the adjustment mechanism is located in an inside of the hole, and both ends of the belt-like component pass through the inside of the hole and penetrate an upper part of the pinching-prevention component, and
    the lower part of the pinching-prevention component and the convex part for pressing the urethra are at positions facing each other with the penis sandwiched in between.

2. The urinary incontinence prevention instrument for males according to claim 1, further comprising:
    a plurality of convex parts for a spacer that are attached to the inner circumference surface side of the annular part to form a gap between the penis and the inner circumference surface side of the annular part.

3. The urinary incontinence prevention instrument for males according to claim 1, wherein the adjustment mechanism changes the length of each of the ends of the belt-like component by a same amount.

4. The urinary incontinence prevention instrument for males according to claim 1, further comprising;
    a cover having an adhesive portion, and being fixed to the pinching-prevention component or the convex part for pressing the urethra by using the adhesive portion.

* * * * *